US012605221B2

(12) United States Patent
Imahiyerobo

(10) Patent No.: US 12,605,221 B2
(45) Date of Patent: Apr. 21, 2026

(54) DISPOSABLE GLOVE DISPENSING SYSTEM

(71) Applicant: Doris Imahiyerobo, Hyde Park, MA (US)

(72) Inventor: Doris Imahiyerobo, Hyde Park, MA (US)

( * ) Notice: Subject to any disclaimer, the term of this patent is extended or adjusted under 35 U.S.C. 154(b) by 189 days.

(21) Appl. No.: 18/411,866

(22) Filed: Jan. 12, 2024

(65) Prior Publication Data

US 2024/0245480 A1    Jul. 25, 2024

Related U.S. Application Data

(60) Provisional application No. 63/440,492, filed on Jan. 23, 2023.

(51) Int. Cl.
| | | |
|---|---|---|
| *A61B 42/40* | (2016.01) | |
| *A61B 42/10* | (2016.01) | |
| *A61B 42/50* | (2016.01) | |

(52) U.S. Cl.
CPC .............. *A61B 42/40* (2016.02); *A61B 42/10* (2016.02); *A61B 42/50* (2016.02)

(58) Field of Classification Search
CPC .................................................... A61B 42/40
See application file for complete search history.

(56) References Cited

U.S. PATENT DOCUMENTS

| | | | |
|---|---|---|---|
| 4,034,853 A | 7/1977 | Smith | |
| 4,773,532 A | 9/1988 | Stephenson | |
| 4,844,293 A | 7/1989 | McLaughlin | |
| 5,025,503 A | 6/1991 | O'Brien | |
| 6,953,130 B2 | 10/2005 | Corbett | |
| 9,931,174 B2 | 4/2018 | Machado et al. | |
| 10,610,319 B2 | 4/2020 | Backhaus et al. | |
| 10,856,707 B2 * | 12/2020 | Peterson ................ A47K 10/32 | |
| 2006/0010563 A1 | 1/2006 | Michel et al. | |
| 2012/0111884 A1 * | 5/2012 | Choi ...................... A61B 90/80 | |
| | | | 222/642 |
| 2012/0259455 A1 | 10/2012 | Balkin et al. | |
| 2016/0152403 A1 | 6/2016 | Ray | |
| 2016/0152430 A1 * | 6/2016 | Ray ......................... A61B 90/98 | |
| | | | 242/563 |
| 2016/0221010 A1 * | 8/2016 | Kurchev ................... B05B 7/02 | |
| 2018/0194539 A1 * | 7/2018 | Ma .......................... A61B 42/40 | |

FOREIGN PATENT DOCUMENTS

| | | |
|---|---|---|
| EP | 1632196 A1 | 3/2006 |
| JP | 2019515155 A | 6/2019 |
| WO | 19970004714 A1 | 2/1997 |

\* cited by examiner

*Primary Examiner* — Gene O Crawford
*Assistant Examiner* — Ayodeji T Ojofeitimi
(74) *Attorney, Agent, or Firm* — McCarter & English, LLP

(57) ABSTRACT

An example package of gloves and associated system is provided. The package of gloves includes two or more gloves, with each of the gloves including a proximal end defining a cuff with an opening capable of receiving a hand of a user therethrough, and a distal end opposing the proximal end and defining finger sections capable of receiving fingers of the hand of the user. The package includes a removable connecting component disposed between each of the respective gloves and connecting the proximal and distal ends of adjacently disposed gloves to each other.

22 Claims, 15 Drawing Sheets

800

804

801

802

803

DISPOSABLE GLOVE DISPENSING SYSTEM

CROSS-REFERENCE TO RELATED APPLICATIONS

This application claims the benefit of a co-pending U.S. Provisional Patent Application No. 63/440,492, which was filed on Jan. 23, 2023. The entire content of the foregoing provisional application is incorporated herein by reference.

TECHNICAL FIELD

The present invention generally relates to a system for dispensing disposable gloves and, particularly, a system that provides for dispensing of disposable gloves in a convenient and clean manner.

BACKGROUND

Surgical or disposable gloves have been used for decades in a variety of industries (e.g., medical, dental, automotive, or the like), as well as for at-home use. Disposable gloves are typically fabricated from a thin, rubber material that provides a tight fitting, thereby protecting the user's hands while maintaining finger dexterity and feel. The low cost of production allows for these gloves to be easily disposed after use.

Disposable gloves are traditionally packaged in a box in a compressed manner, requiring the user to pull the glove out of an opening in the package. In such packaging, multiple gloves are often removed together accidentally, resulting in the user touching the gloves that may be used by a subsequent user. This can be problematic from a cleanliness or bacteria transmission perspective for the subsequent user. For example, in the medical field, the necessity of keeping gloves sterile may be compromised if multiple gloves are dispensed at one time. In addition, due do the compressed packaging of the gloves, the user is typically required to open the wrist section of the glove before the glove can be worn. This may be inconvenient if the user's hands are dirty or only one hand is available to fit the glove over the hand.

SUMMARY OF THE INVENTION

The device and system described herein provides a solution to the shortcomings of traditional systems for dispensing disposable gloves. The system is capable of automatically distributing gloves that can be easily grasped and removed from the dispenser housing without removing the next adjacent glove. The system includes a roll of disposable gloves that are connected via a connection component (e.g., a connecting piece of material) such that the roll can be unwound during removal of a glove from the dispenser housing. In some embodiments, the system includes a fan or alternative air source that is actuated to impart air into the at least partially opened wrist area of the glove, with the air at least partially expanding the glove to provide an opening for easily putting on the glove.

The system therefore provide a means to easily don disposable gloves. In some embodiments, each glove can include a small, expandable plastic ring at the wrist (e.g., molded into the material at the wrist section of each glove) that allows the glove to remain at least partially or slightly open to receive the air from the air source device during distribution. For example, as the next glove to be dispensed is positioned adjacent to the opening of the dispenser housing, the ring at the wrist can bias the wrist area of the glove to at least partially open, creating a space into which air can be blown by the air source device. In such embodiments, the ring at the wrist of the glove can be fabricated from a more rigid material than the glove itself. In some embodiments, the air source device can include a nozzle positioned adjacent to the wrist section of the glove such that (even without a ring at the wrist) the air can enter the glove to at least partially inflate the glove. Such partial inflation results in the glove remaining partially open at the wrist section, allowing the user to easily slip their hand inside. Thus, rather than requiring the user to manage opening of the glove to put their hand inside, the system provides a means for partially inflating and opening the glove for a more convenient positioning of the glove in preparation for placement on the hand of the user.

In some embodiments, the system includes features that allow users to prepare their hands for receiving disposable gloves. The system can includes a replaceable or refillable cylinder of hand treatments—such as a hand sanitizer and/or a moisturizer—that, when activated, is deposited in the user's hands. In some embodiments, the system can include one or more sensors that detect the user's hand adjacent to the dispenser for the hand treatment cylinder or canister, such that the sanitizer or moisturizer is dispensed when the user's hand is detected. The touch-free option allows for dispensing of the sanitizer or moisturizer without requiring the user to physically touch the dispenser.

In some embodiments, the system allows for preparation of a user's hand and dispensing of air and gloves when a user places their hand near the device. For example, when a hand is waved near the hand-treatment delivery sensor, the device activates the dispensing process. As a further example, when a hand is waved near the glove dispenser sensor, the system activates the air flow system that separates and opens the gloves for dispensing. The system can separate and open the gloves, and can position the next available glove at least partially extending out of an opening in the dispenser housing such that the user can either physically remove the glove or place their hand in the glove before separating the glove from the remaining gloves in the housing.

In accordance with embodiments, an exemplary package of gloves is provided. As discussed herein, a "package" of gloves can refer to, e.g., a roll of gloves, a grouping of two or more gloves, or the like. The package of gloves includes a plurality of gloves (e.g., two or more gloves). Each of the plurality of gloves including a proximal end defining a cuff with an opening capable of receiving a hand of a user therethrough, and a distal end opposing the proximal end and defining finger sections capable of receiving fingers of the hand of the user. The package of gloves includes a connecting component disposed between each of the respective gloves of the plurality of gloves and connecting the proximal and distal ends of adjacently disposed gloves to each other.

In some embodiments, the connecting component can connect each of the plurality of gloves to each other such that the plurality of gloves define a substantially continuous structure. In some embodiments, the connecting component can be attached to at least a portion of a perimeter of the cuff at the proximal end and can be attached to at least a portion of the finger sections at the distal end. In some embodiments, a connection of the connecting component to the respective proximal and distal ends can be perforated to allow for separation of the connecting component from the respective glove.

In some embodiments, the connecting component can be attached to only 50% of the perimeter of the cuff at the proximal end. In some embodiments, the connecting component can be attached to about, e.g., 30-80% inclusive, 30-70% inclusive, 30-60% inclusive, 30-50% inclusive, 30-40% inclusive, 40-80% inclusive, 50-80% inclusive, 60-80% inclusive, 70-80% inclusive, 40-70% inclusive, 50-60% inclusive, 30%, 40%, 50%, 60%, 70%, 80%, or the like, of the perimeter of the cuff at the proximal end. In some embodiments, the connecting component can be attached to 100% of the perimeter of the cuff at the proximal end. In some embodiments, the connecting component can be attached to only some of the finger sections at the distal end (e.g., 2 fingers, 3 fingers, 4 fingers, or the like). In some embodiments, the plurality of gloves can be packaged in roll form.

In accordance with embodiments of the present disclosure, an exemplary system for dispensing gloves is provided. The system includes a housing including an opening. The system includes gloves disposed within the housing to allow for selective removal of gloves through the opening of the housing. Each of the gloves includes a proximal end defining a cuff with an opening capable of receiving a hand of a user therethrough, and a distal end opposing the proximal end and defining finger sections capable of receiving fingers of the hand of the use. The system includes a connecting component disposed between each of the gloves and connecting the proximal and distal ends of adjacently disposed gloves to each other.

In some embodiments, the system can include a fan disposed above the gloves and can include a duct pointing towards the gloves to generate air to partially inflate the glove for the user to don. In some embodiments, the fan can be operable on electric power supplied by batteries or an outlet.

In some embodiments, a connection of the connecting component can be perforated to allow for separation of the connection component from the respective glove. In some embodiments, the system can include an actuating unit mounted on an exterior of the housing. In such embodiments, the system can include means for detecting a user, and a driving unit connected to the detecting means and activated by the detecting means upon detection of a user. The fan can be coupled to the driving unit such that activation of the driving unit results in air flow from the fan, thereby partially inflating the glove and rotating the gloves a predetermined rotation such that a user can don the glove. The actuating unit can include a switch means, connected to the driving unit, for deactivating the driving unit after a predetermined amount of time.

In some embodiments, the opening can be positioned at the lower portion of a front of the housing, to facilitate the user donning the glove via a downward motion. In some embodiments, the opening can be positioned at the lower portion of a front of the housing and a bottom of the housing to facilitate the user donning the glove via an upward, leftward, and/or rightward motion relative to the housing. In some embodiments, the system can include at least two containers including hand treatment fluid and capable of being actuated to dispense the hand treatment fluid therefrom. In such embodiments, each of the containers can include an outlet at a bottom of a tubular body, a plunger within the tubular body, a blocking member connected to the plunger, and a securing mechanism on a back of the tubular body, securing the tubular body to an interior back wall of the housing.

In some embodiments, the system can include an actuating unit mounted on an exterior of the housing. The actuating unit can include means for detecting a user, and a driving unit connected to the detecting means and activated by the detecting means upon detection of a user. The tubular body can be coupled electronically to the driving unit such that activation of the driving unit results in reciprocal linear movement of the plunger, thereby moving the blocking member and dispensing a predetermined amount of the hand treatment through the outlet. The actuating unit can include switch means, connected to said driving unit, for deactivating said driving unit when the plunger completes one cycle of the reciprocal linear movement.

In accordance with embodiments of the present disclosure, an exemplary method for dispensing gloves is provided. The method includes at least partially extending a glove from an opening in a housing. The housing includes a plurality of gloves. Each of the plurality of gloves includes a proximal end defining a cuff with an opening capable of receiving a hand of a user therethrough, and a distal end opposing the proximal end and defining finger sections capable of receiving fingers of the hand of the user. The housing includes a connecting component disposed between each of the respective gloves of the plurality of gloves and connecting the proximal and distal ends of adjacently disposed gloves to each other. The method includes separating the glove from the connecting component to fully remove the glove from the housing.

In some embodiments, the method can include motioning a hand in front of an actuating unit of the housing to activate extension of the glove from the housing and to expose a majority of the glove. In some embodiments, the method can include motioning a hand in front of an actuating unit of the housing to dispense a predetermined amount of a hand treatment from a container stored within the housing.

Any combination and/or permutation of embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

To assist those of skill in the art in making and using the disposable glove dispensing system, reference is made to the accompanying figures, wherein.

DETAILED DESCRIPTION

Figure 1:
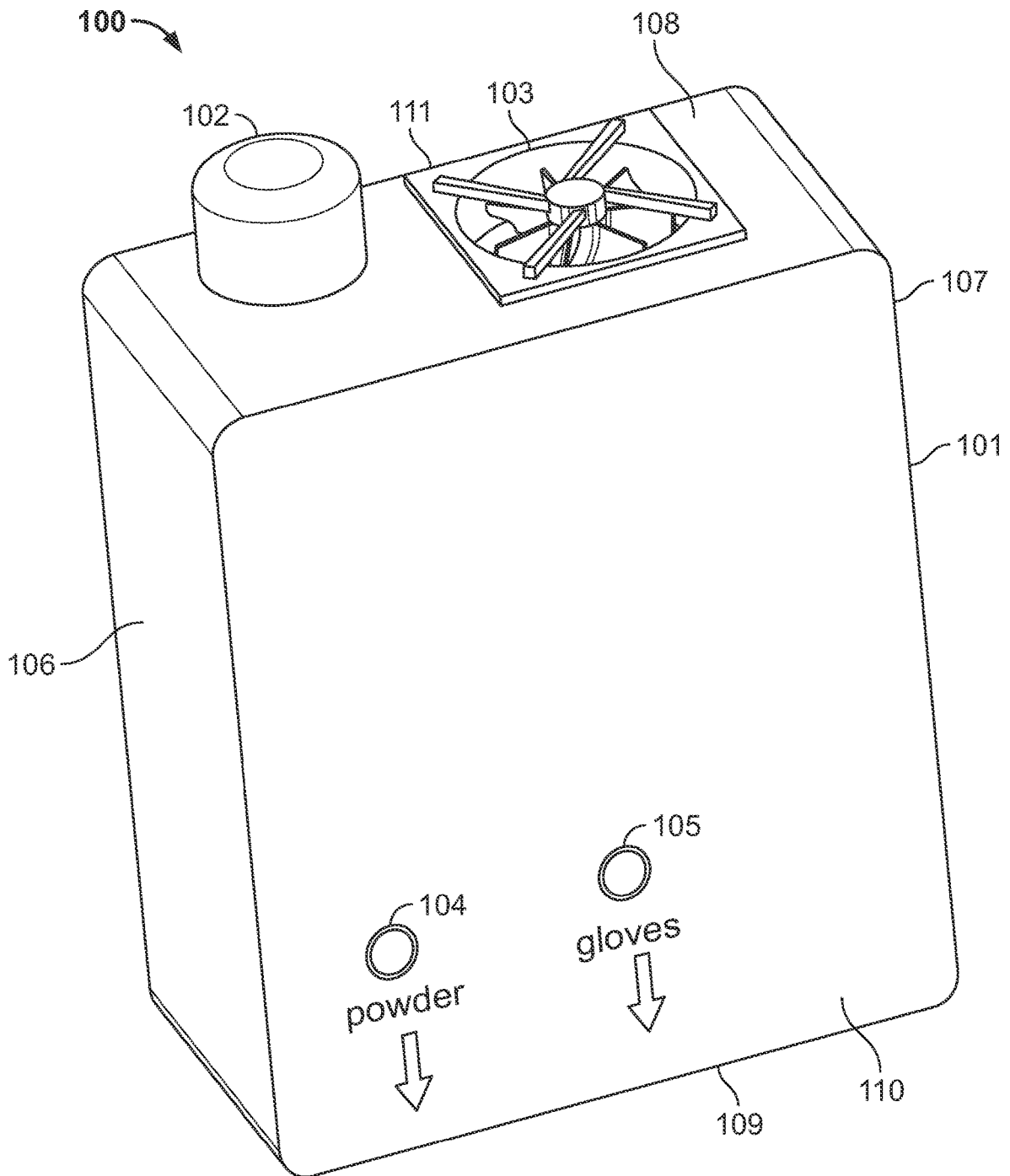
FIG. 1 is a perspective view of an exemplary disposable glove dispensing system of the present disclosure, including a depiction of an exterior of the system with hand-treatment sensors, a glove dispensing sensor, and an air source fan.

As used herein, the directional prepositions of up, upwardly, down, downwardly, front, back, top, upper, bottom, lower, left, right, and other such terms refer to the system as it is oriented and appears in the drawings and are used for convenience only. These designations are not intended to be limiting or to imply that the system has to be used or positioned in any particular orientation. Some embodiments of the system can include similar structures and/or functions. As such, similar reference numbers are used to refer to similar structures.

Figure 2:
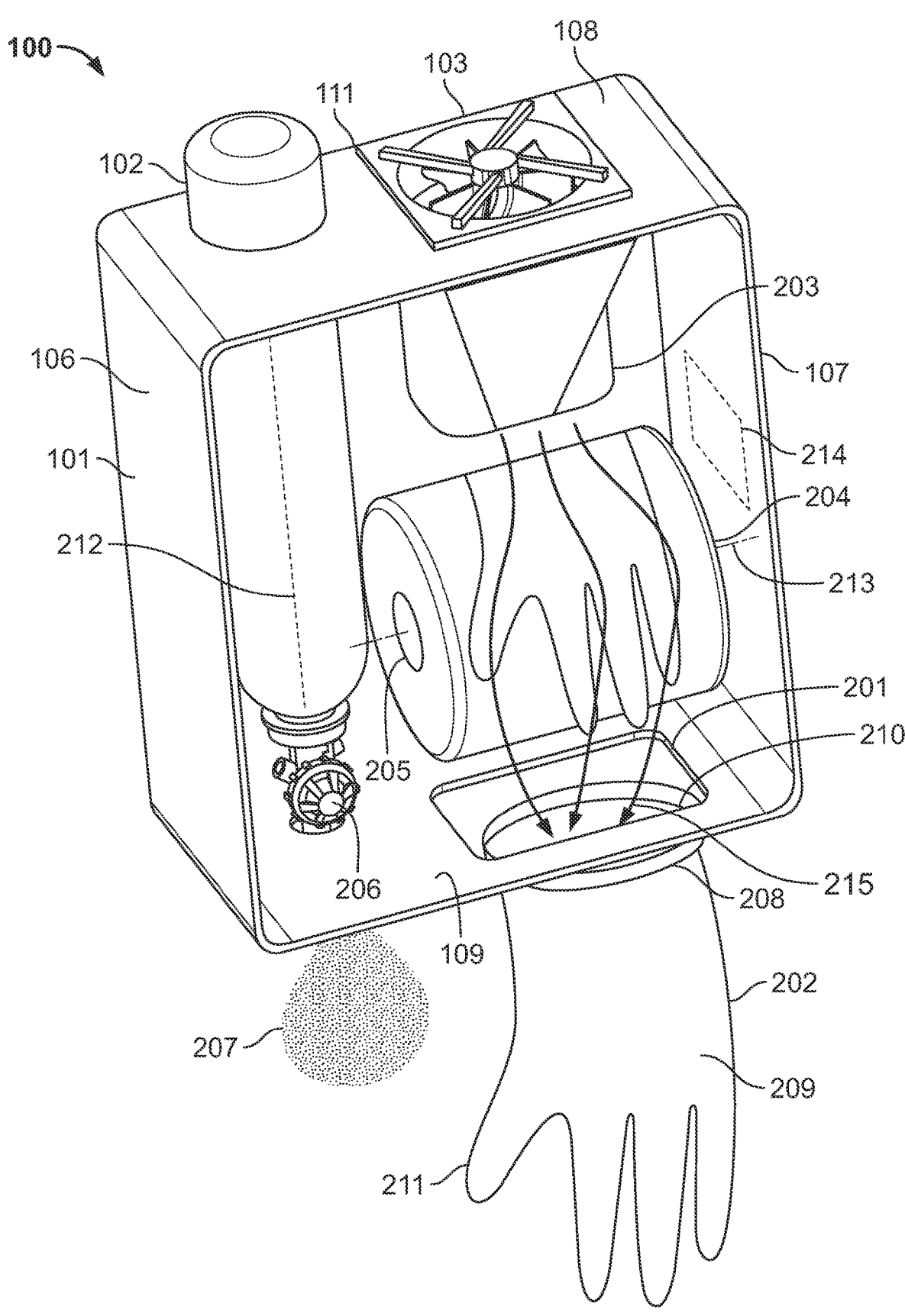
FIG. 2 is a perspective, cross-sectional view of an exemplary disposable glove dispensing system of FIG. 1, illustrating an interior of the system with a cylinder containing the hand-treatment fluid, a roll of disposable gloves disposed within a housing, a housing opening through which the glove is dispensed, and the air source fan.
Figure 3:
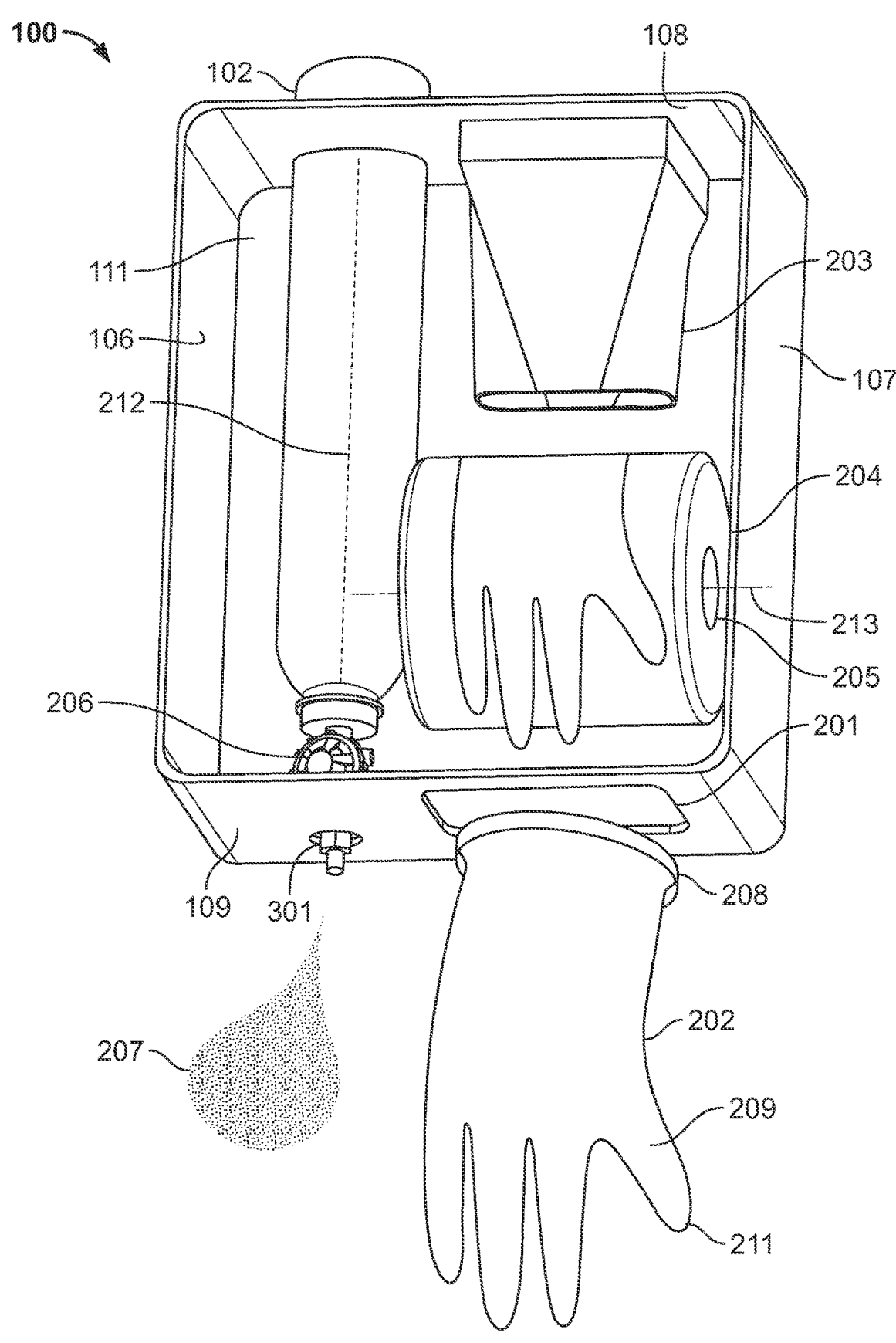
FIG. 3 is a perspective, cross-sectional view of an exemplary disposable glove dispensing system of FIG. 1, illustrating an interior of the system with a cylinder containing the hand-treatment fluid, a roll of disposable gloves disposed within a housing, a housing opening through which the glove is dispensed, and the air source fan.

FIGS. 1-3 show various perspective views of a disposable glove dispensing system 100 (hereinafter "system 100"). The system 100 includes a housing 101 with a back surface 111, a first side surface 106, a second side surface 107, a top surface 108, a bottom or base surface 109, and a front surface 110. The housing 101 is configured to at least partially retain and protect internal components discussed herein, and is capable of being selectively mounted to a wall or other similar structure. The outer portion of the housing 101 can include one or more a hand-treatment sensors 104 and a glove dispensing sensor 105. In some embodiments, the sensors 104, 105 can be infrared near-motion detection sensors, photo sensors, or the like. Placing a user's hand in front of the sensor 104 dispenses powder, moisturizer and/or hand sanitizer out of the base surface 109 of the housing 101. Placing a user's hand in front of the sensor 105 dispenses a glove out of the base surface 109 of the housing 101.

For example, the housing 101 can include a cylinder or container 102 that includes dispensing hand-treatments, such as moisturizer and/or hand sanitizer 207. Activation of the sensor 104 can activate a solenoid 206 to dispense the hand-treatment. Activation of the sensor 105 can activate a glove dispensing mechanism within the housing 101 to dispense a predetermined length of a glove 202 from the base surface 109. The dispensing mechanism can include an electric circuitry for controlling operation of the dispensing mechanism. The container 102 can be replaceable or refillable (and in some embodiments removable from the housing 101). The top surface 108 of the housing 101 can include a fan 103 capable of being actuated to introduce air into the housing 101 through an air duct 203 (see FIG. 3). The air duct 203 is positioned within the interior of the housing 101 with one end connected to the fan 103 and the opposing end formed and directed towards gloves for introducing air into the next glove to be dispensed. In some embodiments, the air duct 203 can have a truncated-cone shape that is substantially cylindrical. For example, the air duct 203 can have a main body and a tapered portion having a truncated-cone shape. The main body near the fan 103 can define a greater internal diameter or cross-sectional area, while the tapered portion can define a smaller internal diameter or cross-sectional area to increase the air flow velocity directed into the glove to be dispensed. One of ordinary skill in the art would appreciate that the air duct 203 can be designed in any number of configurations, and embodiments of the present invention are contemplated for use with any such configuration.

With reference to FIG. 3, the internal components of the system 100 include a glove cartridge 204 (e.g., package, roll, or the like) including multiple gloves 202 rolled around a center support 205 (e.g., a cylindrical rod, or the like). The cartridge 204 is mounted within the housing 101 such that the cartridge 204 can rotate about a central longitudinal axis 213 of the support 205. The central longitudinal axis 213 can be oriented substantially perpendicularly relative to the direction of dispensing of the gloves 202. In some embodiments, the system 100 can include an actuator 214 configured to drive rotation of the cartridge 204 about the central longitudinal axis 213 of the support 205. In some embodiments, the airflow from the fan 103 can drive rotation of the cartridge 204 about the central longitudinal axis 213 of the support 205. For example, the airflow can push against the gloves 202 wrapped around the central support 205 to force rotation of the cartridge 204. In some embodiments, the air duct 203 can be offset or angled relative to the central longitudinal axis 213 to assist with rotation of the cartridge 204.

In some embodiments, the actuator 214 and fan 103 can operate in conjunction, such that actuator 214 positions the cartridge 204 in an ideal position for the fan 103 and air duct 203 to direct air into the wrist section 208 of the glove 202. For example, the actuator 214 can rotate the cartridge 204 to a position where the wrist section 208 of the glove 202 is positioned directly below the opening of the air duct 203 such that air is directed into the glove 202 for expansion (and in some embodiments rotation of the cartridge 204 to dispense the glove 202 from the housing 202). The air duct 203 can be positioned immediately adjacent to or over the cartridge 204 such that airflow from the air duct 203 can at least partially enter the opening at the wrist section 208 of the glove 202. In some embodiments, the air duct 203 can direct airflow substantially perpendicularly relative to the central longitudinal axis 213 of the support 205. In some embodiments, the air duct 203 can direct airflow at an angle relative to the central longitudinal axis 213 of the support 205.

In some embodiments, the air duct 203 can be oriented to direct airflow into the opening of the glove 202 from a position, e.g., above the support 205, below the support 205, to the left of the support 205, to the right of the support 205, or the like. In some embodiments, the air duct 203 can direct airflow at an angle of about, e.g., 10-80 degrees inclusive, 10-70 degrees inclusive, 10-60 degrees inclusive, 10-50 degrees inclusive, 10-40 degrees inclusive, 10-30 degrees inclusive, 10-20 degrees inclusive, 20-80 degrees inclusive 30-80 degrees inclusive, 40-80 degrees inclusive, 50-80 degrees inclusive, 60-80 degrees inclusive, 70-80 degrees inclusive, 10 degrees, 20 degrees, 30 degrees, 40 degrees, 50 degrees, 60 degrees, 70 degrees, 80 degrees, or the like, tangentially relative to the central longitudinal axis 213 of the support 205. The system 100 includes a glove dispensing opening 201 formed at the bottom surface 109 of the housing 101. The opening 201 can be aligned with (or substantially aligned with) the fan 103 on the opposing side of the housing 101 to ensure that airflow from the fan 103 directs dispensing of at least a portion of the glove 202 through the opening 201.

Each glove 202 includes a wrist section 208 in the form of an oval or circle, or the like. The wrist section 208 can be formed from a small, plastic, foldable ring molded on a main body 209 of the glove 202. In some embodiments, the ring can be formed from a different (e.g., more rigid) material than the body of the glove 202. In some embodiments, the ring can be formed from multiple layers of the same material used to fabricate the glove 202. When a glove 202 is partially unrolled from the cartridge 204 or positioned as the next glove 202 to be dispensed, the wrist section 208 can spring open (either partially or fully) to accept air from the fan 103. In particular, the wrist section 208 can at least partially expand to open the opening 210 (FIG. 2) extending into the main body 209 of the glove 202. This ensures that airflow from the fan 103 will at least partially enter into the main body 209 through the opening 210.

In some embodiments, partial inflation can result in the main body 209 being at least partially inflated or expanded without inflation of the finger sections 211. In some embodiments, partial inflation can result in the main body 209 and at least some of the finger sections 211 of the glove 202 being partially inflated or expanded. The system 100 can include an onboard microcontroller or processor that governs all sensor and delivery activities therein. For example, the microcontroller or processor can regulate the flow rate created by the fan 103, the rotation speed and angular position of the cartridge 204, or the like. The system 100 has power options that include but are not limited to 120V household current, rechargeable batteries, or the like. In some embodiments, the system 100 can include wireless and/or WiFi connectivity for monitoring air and glove supply status and/or to notify users when refilling is required. In some embodiments, an indicator (e.g., an LED light, or the like) disposed on the outside of the housing 101 can be actuated to visually alert users when refilling of the cartridge 204 is required.

FIGS. 2-3 show the interior perspective of the disposable glove dispensing system 100. Within the housing 101 are a plurality of gloves 202 disposed around a center support 205. The gloves 202 are dispensed through the opening 201 formed on the bottom surface 109 of the housing 101, e.g., near the bottom edge of the front surface 110. The glove 202 is dispensed in a vertical, hanging orientation through the opening 201, finger sections 211 first, such that the user can move their hand in a downward direction into the glove 202 through the opening 210. The fan 103 is positioned directly above the roll of gloves 202. When the fan 103 is activated to blow air through the air duct 203, air is blown into the open wrist section 208 of the glove 202 to partially inflate the glove 202 and allow the user to easily slip their hand inside. In some embodiments, air is blown through the opening 210 and into the wrist section 208. In some embodiments, air is blows into the wrist section 208 before the glove 202 is fully dispensed through the opening 201. Arrows 215 in FIG. 2 indicate the direction of the air flow from the duct 203. In some embodiments, the system 100 can include one cylinder 102 to dispense a hand-treatment 207. Upon activation by the hand treatment sensor 104, the sensor 104 activates the solenoid 206 to open the cylinder 102 to initiate dispensing of a hand treatment 207. A plunger 212 located within the cylinder 102 can move a predetermined distance to dispense a certain amount of the hand treatment each time.

Figure 4:
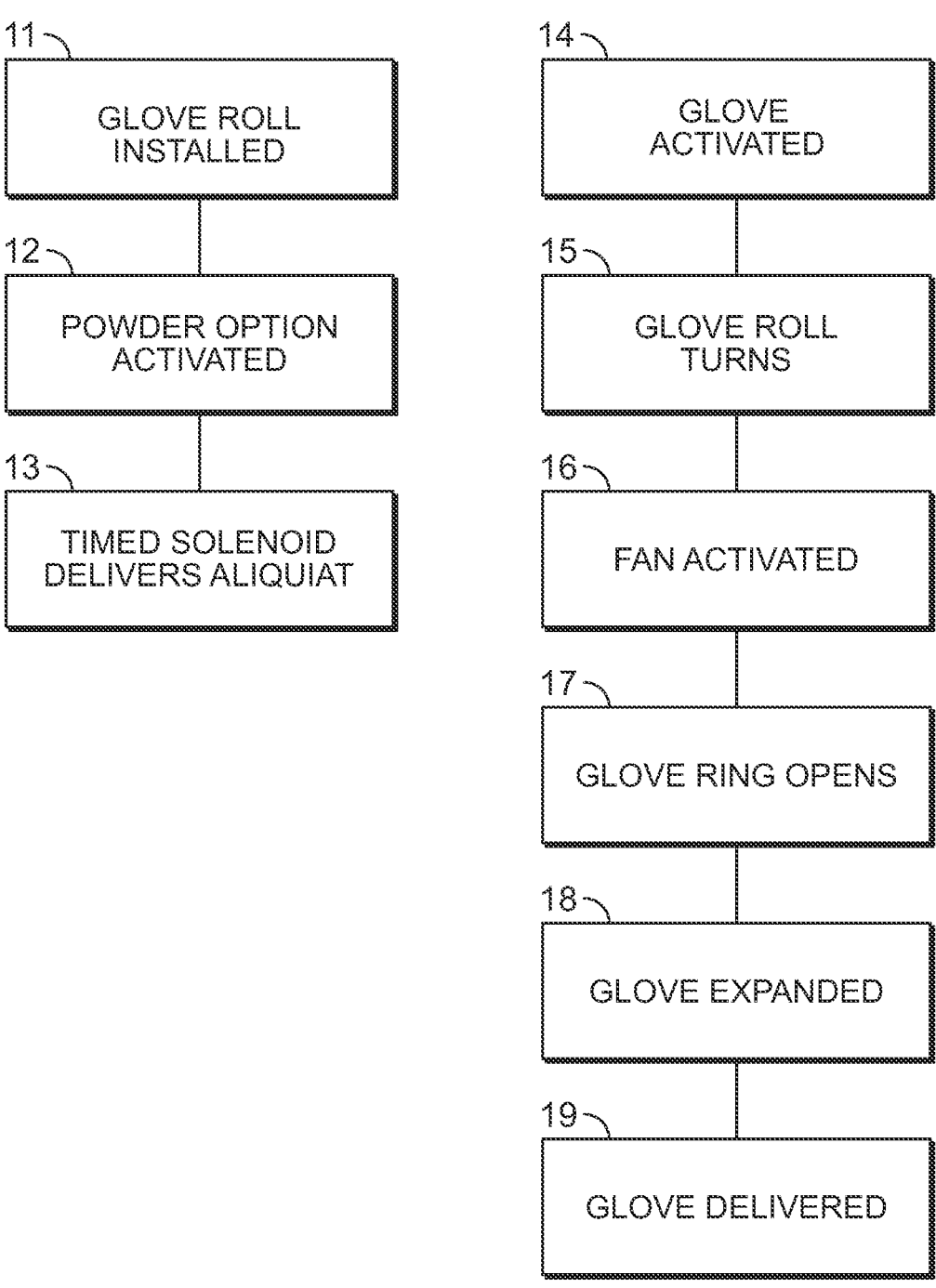
FIG. 4 is a flowchart illustrating a process of using an exemplary disposable glove dispensing system.

FIG. 4 is a flowchart illustrating a process of using a system 100. At step 11, the glove cartridge (e.g. package, roll, or the like) is installed in the housing. At step 12, the hand-treatment option can be optionally activated (e.g., hand or object moved in front of or over the hand-treatment sensor) and, at step 13, a solenoid opens the cylinder momentarily as instructed by the microcontroller to deliver an aliquot of hand sanitizer and/or moisturizer to the user. At step 14, rotation of the glove cartridge can be activated by a hand or object moving in front of or over the glove dispensing sensor, with the glove rotating as instructed by the microcontroller to position the cuff of a glove in an optimal position under the fan (step 15). Upon positioning of the glove in the desired radial position, at step 16, the fan is activated as instructed by the microcontroller to deliver air to partially inflate the glove. The air introduced into the glove causes the cuff to open (step 17) and the glove is expanded (step 18) for easy insertion of the user's hand into the glove. After at least partially positioning the user's hand into the glove, the glove can be separated from the system (step 19), e.g., from the remaining gloves in the housing.

Figure 5:
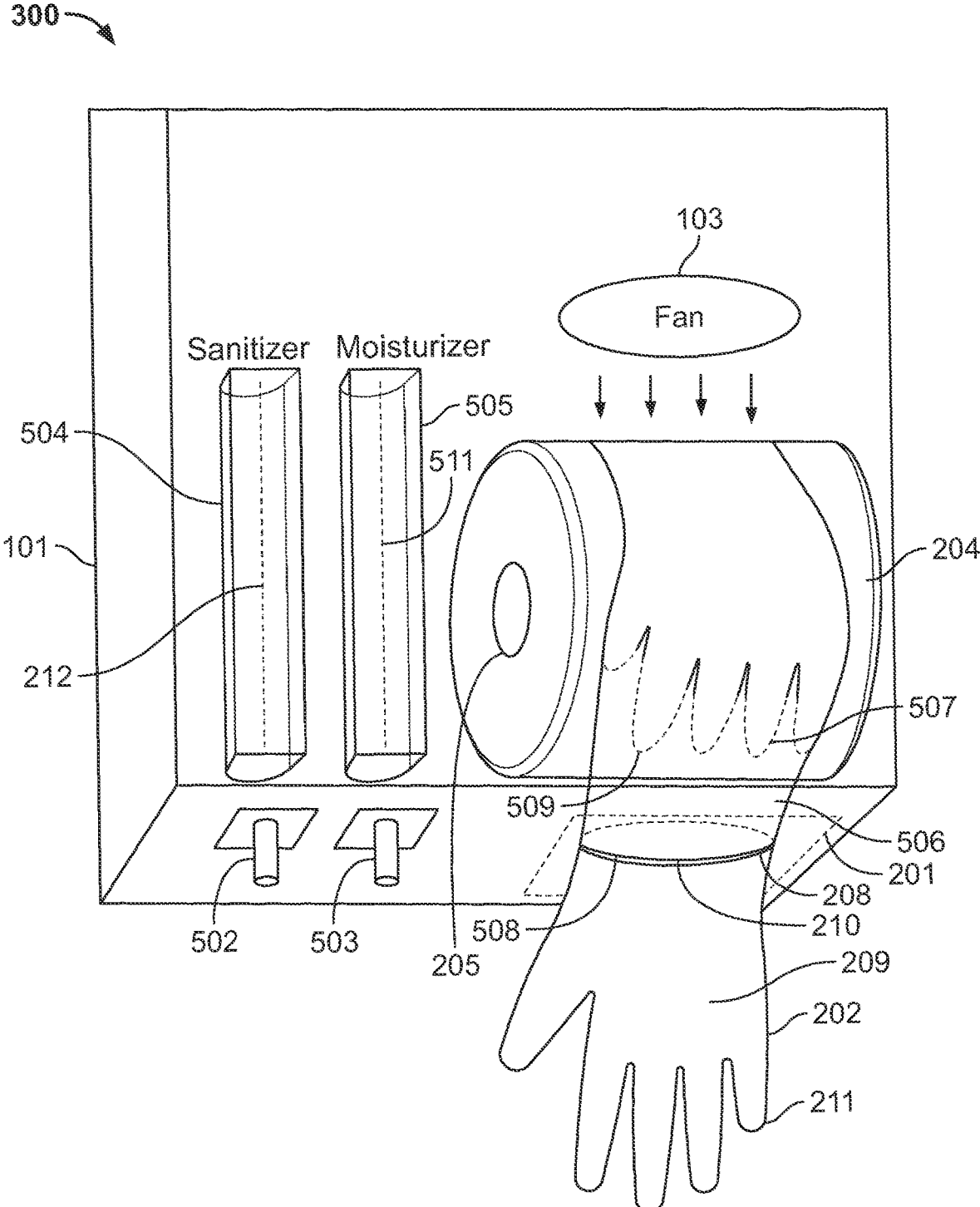
FIG. 5 is a diagrammatic view of an exemplary disposable glove dispensing system showing an interior of a housing with two cylinders for hand treatment fluid.

FIG. 5 shows another embodiment of a disposable glove dispensing system 300. The system 300 can be substantially similar in structure and/or function to the system 100, except for the distinctions noted herein. In some embodiments, one or more portions of the system 300 can be incorporated into the system 100. The housing 101 includes an outer portion, including a back surface, a first side surface, a second side surface, a top wall, a bottom or base surface, and a front surface. The front surface can include a hand-treatment sensor(s) and a glove dispensing sensor in the form of infrared near-motion detection sensors or photo sensors (not shown). Rather than a single cylinder, the system 300 can include two individual cylinders 504, 505 for independently dispensing of hand-treatments, such as moisturizer and/or hand sanitizer. The system 300 includes a roll 204 of gloves 202 disposed around a center support 205. The system 300 includes a dispensing opening 201 formed in the housing 101, and fan 103 disposed over the roll 204.

The pre-rolled glove cartridge 204 is in the form of a continuous roll of a plurality of gloves 202. The plurality of gloves 202 are sequentially connected to each other (e.g., end-to-end) via a connecting material or component 506. The connecting component 506 is attached to the cuff or wrist section 208 of a glove 202 about to be dispensed from the housing 101, and the finger sections 211 of the next adjacently positioned glove 202. In particular, the connecting component 506 includes one edge or end 508 that is at least partially connected to the wrist section 208 of the glove 202, and an opposing edge or end 509 that is at least partially connected to the finger sections 211 of the next glove 202. In some embodiments, the entire cuff 208 can be attached to the connecting component 506. In some embodiments, only the palmar or dorsal cuff 208 at the proximal end side can be attached to the connecting component 506.

In some embodiments, the connecting component 506 can be a single sheet of material that connects along at least a portion of the wrist section 208 and along at least a portion of the finger sections 211. In some embodiments, the connecting component 506 can define a substantially circular or oval configuration at the end 508 connecting to the wrist section 208 such that the connecting component 506 can connect to the entire perimeter edge of the wrist section 208. In such embodiments, the connecting component 506 can narrow or join at the end 509 such that the end 509 defines a single line of connection along the finger sections 211. The connecting component 506 connects to the wrist section 208 and finger sections 211 along connection points 507. These connection points 507 can be perforated to allow for easy separation.

In some embodiments, the connecting component 506 can connect to the wrist section 208 by about, e.g., 50-100% inclusive, 50-90% inclusive, 50-80% inclusive, 50-70% inclusive, 50-60% inclusive, 60-100% inclusive, 70-100% inclusive, 80-100% inclusive, 90-100% inclusive, 60-90% inclusive, 70-80% inclusive, 50%, 60%, 70%, 80%, 90%, 100%, or the like, of the perimeter of the wrist section 208. In some embodiments, the connecting component 506 can connect to only the rear side of the wrist section 208 (e.g., the side furthest from the user to allow for placement of the user's hand into the glove). In such embodiments, the connecting component 506 defines a planar sheet of material, i.e., not circular or oval. In such embodiments, the connecting component 506 can connect to the rear side of the wrist section 208 by about, e.g., 50-100% inclusive, 50-90% inclusive, 50-80% inclusive, 50-70% inclusive, 50-60% inclusive, 60-100% inclusive, 70-100% inclusive, 80-100% inclusive, 90-100% inclusive, 60-90% inclusive, 70-80% inclusive, 50%, 60%, 70%, 80%, 90%, 100%, or the like, of the rear side perimeter of the wrist section 208. For example, in some embodiments, only a portion of the perimeter of the wrist section 208 can be connected to the connecting component 506 (e.g., a continuous connection inclusive of perforations formed along the connection points 507).

In some embodiments, the connecting component 506 can connect to the finger sections 211 by about, e.g., 50-100% inclusive, 50-90% inclusive, 50-80% inclusive, 50-70% inclusive, 50-60% inclusive, 60-100% inclusive, 70-100% inclusive, 80-100% inclusive, 90-100% inclusive, 60-90% inclusive, 70-80% inclusive, 50%, 60%, 70%, 80%, 90%, 100%, or the like, of the edge along the finger sections 211. For example, in some embodiments, the connecting component 506 can be connected to the finger sections 211 only at each of the edges or tips of the fingers, with these connecting points 507 including perforations. In some embodiments, the perforated connection points 507 can be along the entire edge of the finger sections 211. In some embodiments, the connecting component 506 can be connected to only some of the finger sections 211, for example 2 of 5 fingers, 3 of 5 fingers, 4 of 5 fingers, or the like. In some embodiments, the connecting component 506 can be connected to only one or more of the fingertip portions of the finger sections 211. In some embodiments, the material forming the finger sections 211 can be thicker to prevent accidental tears of the finger sections 211 when removing the connecting component 506.

The connection point(s) 507 of the connecting component 506 at edges 508, 509 are perforated to allow for easy separation once the user dons the glove 202. The percentages of connection between components noted above are intended to represent the overall circumference of the perimeter of the wrist section 508 (unless specified as indicating only the rear section of the wrist section 508) or the edge along the finger sections 211 that is connected to the perforated connecting points 507 (e.g., a percentage of the circumference having both perforated and non-perforated sections), and are not intended to include the lack of connection in the perforated areas. For example, when referring to connection to 50% of the wrist section 208 perimeter, this value is intended to represent only half of the perimeter being coupled to the connecting component 506 (inclusive of the perforated area which is connected and the space defined between the connection points).

In some embodiments, the density of the perforations (e.g., the number of perforations, the size of each perforation/opening, and/or the spacing between perforations along the connecting edge 508, 509 of the connecting component 506) can be varied to ensure easy separation of the glove relative to the connecting component 506 without damaging the glove 202. For example, in some embodiments, the density of the perforations along the finger sections 211 can be higher than the density of the perforations along the wrist section 208 (e.g., more perforations or larger sized perforations at the finger sections 211) to provide a stronger connection at the wrist section 208 and a weaker connection at the finger sections 211, allowing for easier separation of the connecting component 506 at the finger sections 211. The higher density of perforations can require less force when detaching the connecting component 506 from the finger sections 211. In some embodiments, the density of perforations at the finger sections 211 and the wrist section 208 can be the same. The perforations advantageously provide additional space for the passage of air for partial inflation of the glove 202, provides separation between the gloves 202, and limit a first user from touching the next glove 202 in the dispenser during separation. This enables to the gloves 202 to remain sanitary for the second user. The plurality of gloves 202 is a continuous piece, stored in roll form, connected via a perforated intermediary material along different percentages of the perimeter of the cuff of the glove 202. In some embodiments, only the palmar or dorsal cuff side is attached to the connecting component 506 such that when the fan 103 is activated, air will enter the open cuff. In some embodiments, the connecting component may be connected to 25%, 30%, 35%, 40%, 45%, 50%, 55%, 60%, 65%, 70%, 80%, or 90%, of the cuff of the glove 202.

In some embodiments, the connecting component 506 can be connected to each of the finger sections 211 along the entire finger areas at perforated edges. In some embodiments, the connecting component 506 can be connected to two, three, or four of the finger sections 211. In such embodiments, the two, three or four finger sections 211 can be any combination of the five finger sections 211.

Once the glove dispensing sensor 105 is activated, an actuating system turns on the fan 103 for a predetermined amount of time (e.g., 1 second, 2 seconds, 3 seconds, 4 seconds, 5 seconds, 10 seconds, or the like). The air will partially inflate the glove 202 to allow for easy insertion of the user's hand. The glove 202 can be at least partially extended from the housing 101 such that the opening 210 at the wrist section 208 is exposed and available for the user to insert their hand into the glove 202 through the wrist section 208. For example, the connecting component 506 can be dimensioned long enough to allow the wrist section 208 of the glove 202 to be extended from the housing 101 (such that the user can insert their hand into the glove 202), while maintaining the next glove 202 stored entirely within the housing 101 (i.e., not extending from the opening 201 in the housing 101). This ensures that the next glove 202 to be dispensed is maintained in a sterile or clean environment and is not contaminated by the previous user. Upon insertion of the user's hand into the glove 202, a pulling and/or twisting force can disconnect or tear the glove 202 from the edge 508 of the connecting component 506, and the system 300 can be ready for dispensing of the next glove 202.

In some embodiments, a pulling and/or twisting force can disconnect or tear the connecting component 506 at the edge 509 from the finger sections 211 of the next glove 202, and the system 300 can be ready for dispensing of the next glove 202. The connecting component 506 can be removed from the next glove 202 by either the first user or the second user. For example, the first user could apply a pulling and/or twisting force to disconnect or tear the connecting component 506 from the finger sections 211 of the next glove after donning the glove 202. As another example, the second user could apply a pulling and/or twisting force to disconnect or tear the connecting component 506 from the finger sections 211 before or after donning the next glove 202, if the first user did not remove the connecting component 506 already. In some embodiments, the system 300 can include an internal mechanism that separates the connecting component 506 from the next glove 202 to be dispensed. The perforation density at the connection edge 509 between the connecting component 506 and finger sections 211 and/or wrist section 208 noted above are intended to allow for easier separation of the connecting component 506 from the glove 202 by requiring less pulling and/or twisting force.

In some embodiments, the user inserts their hand into a glove 202 in a downward motion. In some embodiments, once the hand treatment sensor 104 is activated, the solenoid opens and a plunger 212, 511 compresses the hand treatment stored within the appropriate cylinder 504, 505 a predetermined distance, thereby dispensing a predetermined amount of the hand treatment out of opening 502, 503. In some embodiments, the hand treatment can be performed prior to putting on a glove 202. In some embodiments, the hand treatment can be used by the user after the glove 202 has been placed over the hand for additional reassurance of cleanliness.

Figure 6:
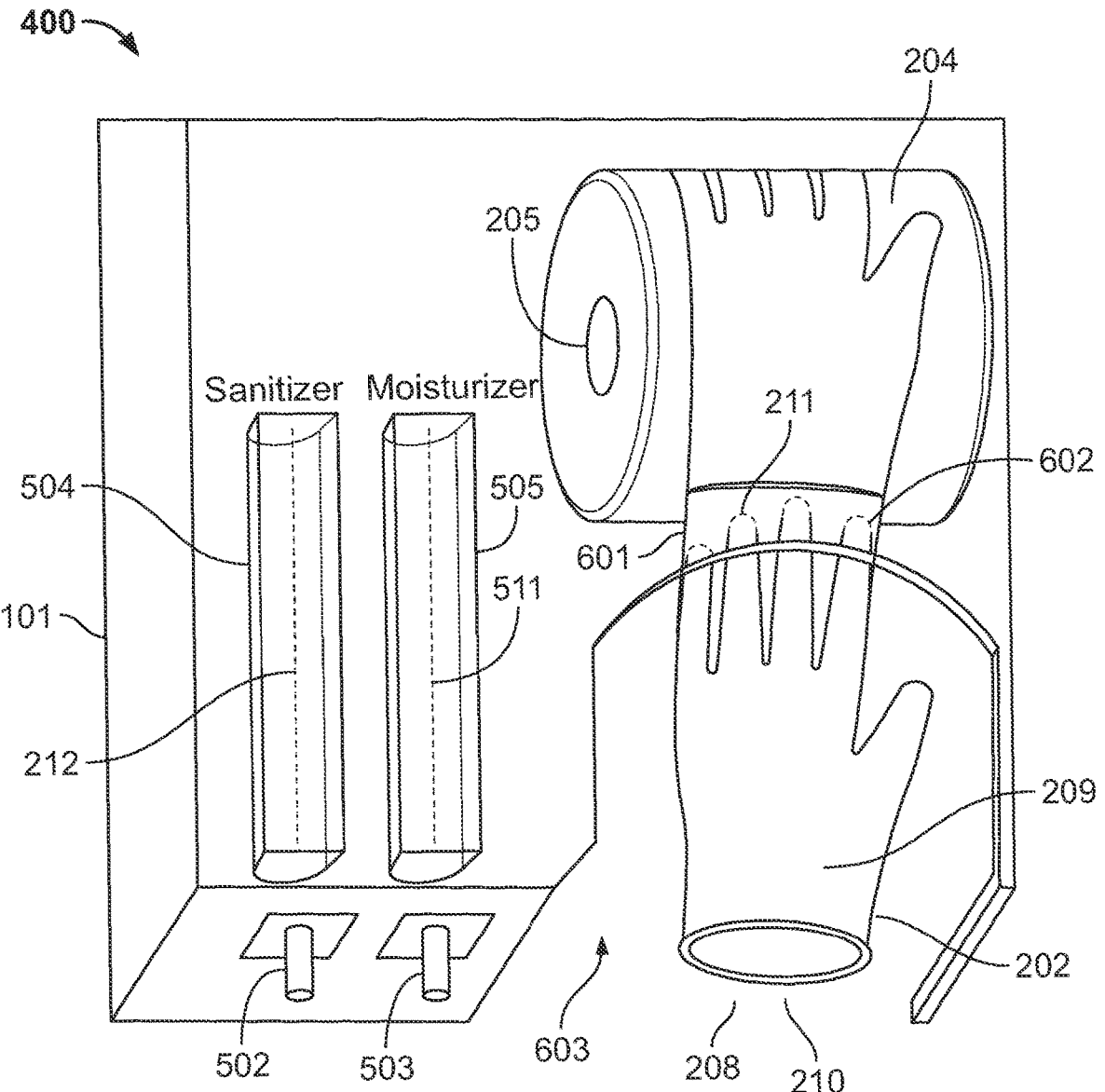
FIG. 6 is a diagrammatic view of an exemplary disposable glove dispensing system of the present disclosure.

FIG. 6 is a diagrammatic view of a disposable glove dispensing system 400. The system 400 can be substantially similar to the systems 100 and/or 300, except for the distinctions noted herein. The system 400 includes a housing 101 comprising a back surface, a first side surface, a second side surface, a top wall, a bottom or base surface, a front surface, and an opening 603. The opening 603 is positioned on the lower edge of the front surface and extends to the bottom surface, thereby encompassing the front, lower corner of the housing 101. The orientation of the gloves 202 of the roll 204 are in the opposite direction from the gloves 202 in the system 300 of FIG. 5. In particular, the wrist section 208 of the gloves 202 faces downward toward and/or through the opening 603 at the bottom wall of the housing 101. The connecting component 601 can be substantially similar to the connecting component 506, including the different percentages of connection relative to the wrist section 208 and/or the finger sections 211 (e.g., the proximal end of the wrist section 208 and the distal end of the finger sections 211). Connection points 602 of the connecting component 601 are perforated to allow for easy separation once the user dons the glove 202.

In some embodiments, only the palmar or dorsal cuff at the proximal end side can be attached to the connecting component 601. In some embodiments, the entire perimeter of the cuff or wrist section 208 of the proximal side can be attached to the connecting component 601. In some embodiments, all five finger sections 211 can be attached to the connecting component 601. In some embodiments, less than all five finger sections 211 can be attached to the connecting component 601. The plurality of gloves 202 are dispensed from the opening 603 in the housing 101 in a cuff first orientation. This orientation can create a larger opening at the wrist section 208 such that the user inserts their hand into a glove 202 in an upward motion. In some embodiments, the system 400 can operate without a fan and partial inflation of the glove 202. In some embodiments, the downward motion of the glove 202 during dispensing of the opening 603 can at least partially inflate the glove 202 at the wrist section 208.

Figure 7:
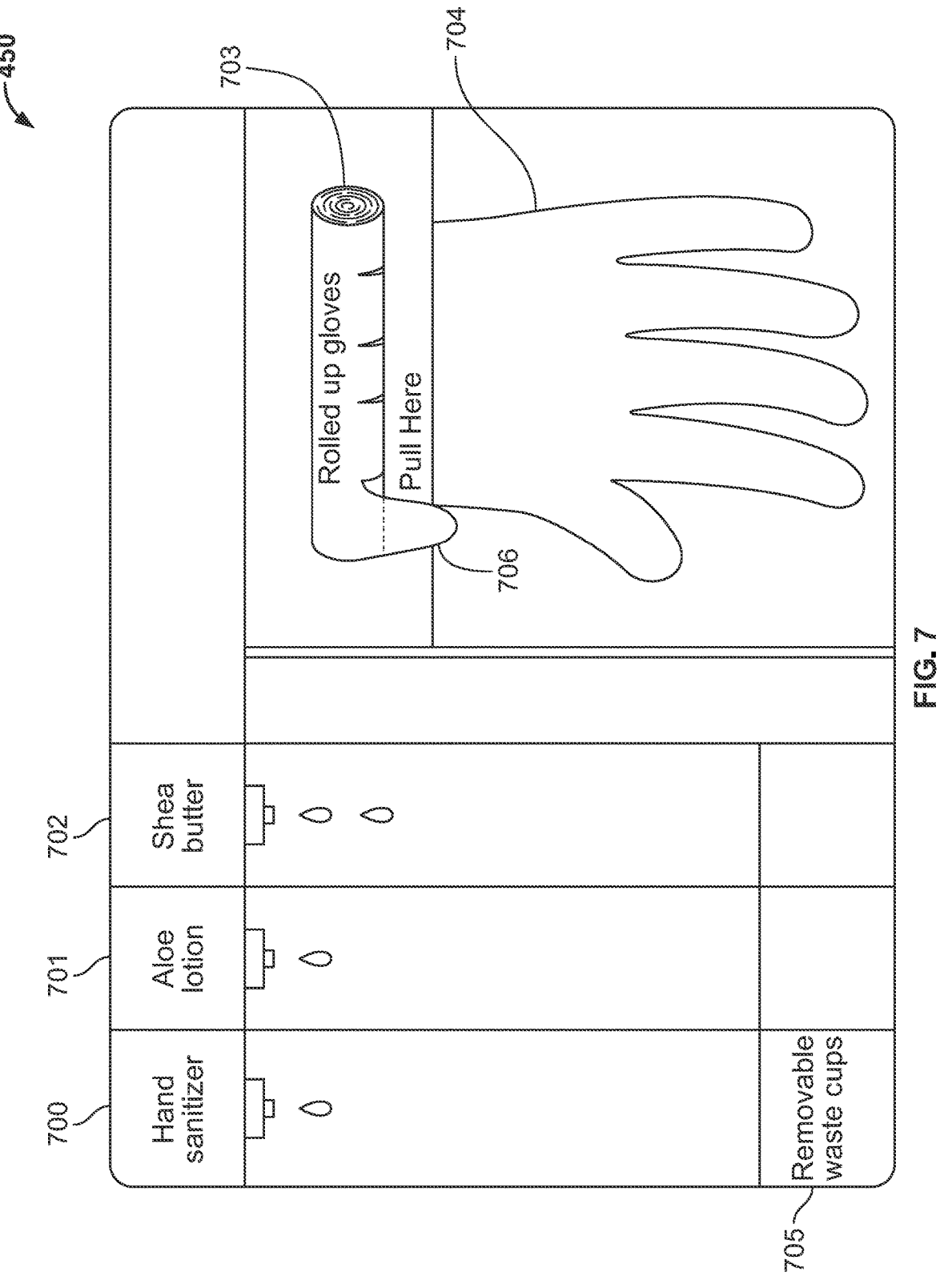
FIG. 7 is a diagrammatic view of an exemplary disposable glove dispensing system of the present disclosure.

FIG. 7 is a diagrammatic view of a disposable glove dispensing system 450. The system 450 can be substantially similar to the system 400, except for the distinctions noted herein. The system 450 includes three cylinders 700, 701, 702 containing hand treatments (as compared to the one or two cylinder versions previously discussed). The system 450 includes a plurality of gloves 704 in roll 703 form. The pre-rolled glove cartridge is a continuous roll 703 of a plurality of gloves 704. The plurality of gloves 704 can be connected via a connecting component (not shown). In the system 450 of FIG. 7, the glove 704 is dispensed mechanically by the user. For example, one or more of the fingers of the glove 704 can be exposed through an opening in the housing such that the user can pull on the fingers to dispense the glove 704. Once the glove 704 has been unrolled, the user can separate the glove 704 from the plurality of gloves 703 along the connection point of the connecting component. In some embodiments, the end of the glove 704 can include a pull tab 706 or one of the finger sections can act as a pull tab 706 for mechanically pulling on the glove 704 during dispensing. In some embodiments, the system 450 can include reusable waste cups 705.

Figure 8:
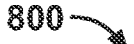
FIG. 8 is a diagrammatic view of an exemplary disposable glove dispensing system of the present disclosure.

FIG. 8 is a perspective view of a disposable glove dispensing system 800. The system 800 includes a housing 801, an opening 802 formed at the front surface of the housing 801, a stack of gloves 803 disposed within the housing 801, a securing mechanism (not shown) securing the stack of gloves 803 inside the housing 801, and an attachment mechanism 804 to secure the housing 801 onto a wall. In some embodiments, the opening 802 can be located at approximately the center of the front wall of the housing 801. In some embodiments, the opening 802 can be located to the left or right of the front wall of the housing 801. The stack of gloves 803 can be oriented vertically with the finger sections pointing downwards. A portion of the stack of gloves 803 can be exposed through the opening 802 while the remainder of the stack of gloves 803 can be disposed within the housing 801. To don the gloves 803, the user moves their hand downward into the glove 803 and pulls the glove 803 away from the stack once their hand is inserted. The gloves 803 can be secured to each other at the wrist sections such that once the user places their hand inside of the glove 803, a twisting or pulling motion separates the worn glove 803 from the remaining gloves 803 in the housing 801.

Figure 9:
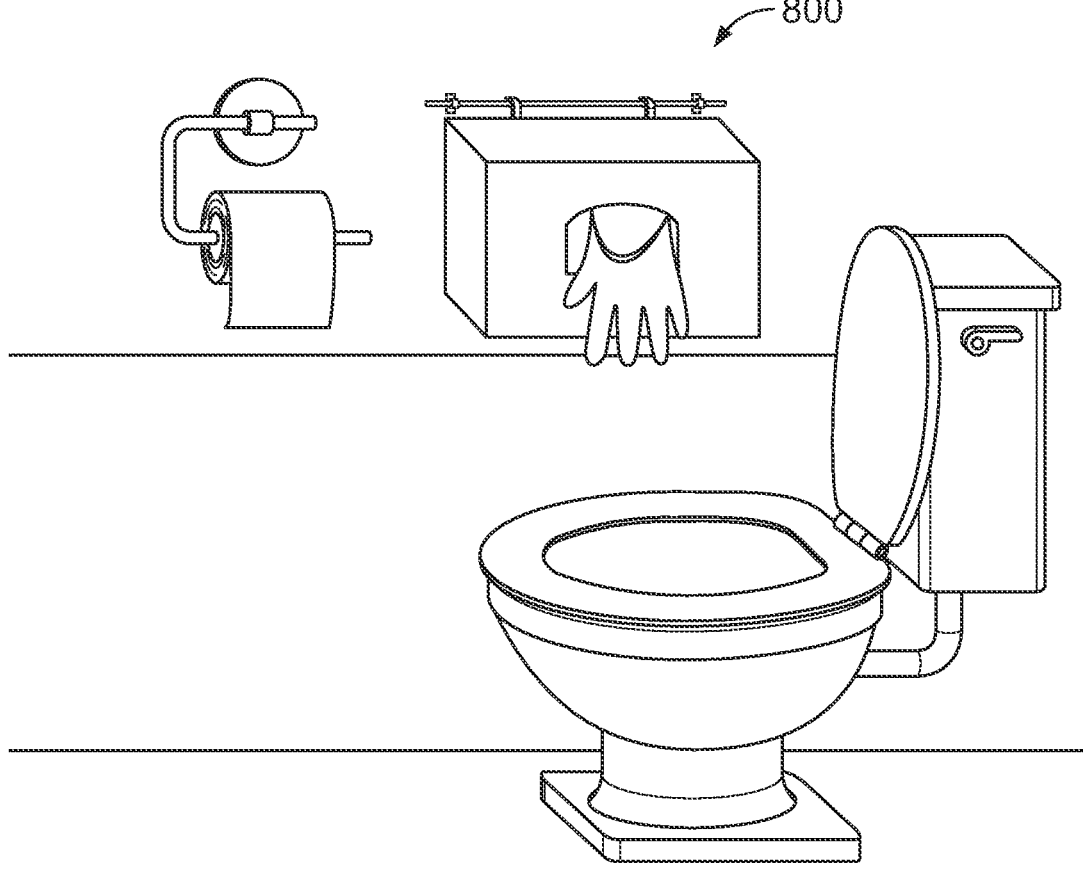
FIG. 9 is a diagrammatic view of an exemplary disposable glove dispensing system of FIG. 8 mounted to a wall.

FIG. 9. illustrates how the disposable glove dispensing system 800 can be installed on a wall of a restroom. The disposable glove dispensing system 800 can be secured on the wall by the attachment mechanism 804 (e.g., hooks, screws, or the like). The disposable glove dispensing system 800 can be located near the toilet or anywhere else that is desirable in the restroom. One of ordinary skill in the art would appreciate that the attachment mechanism 804 could be designed in any number of configurations, and embodiments of the present invention are contemplated for use with any such configuration.

Figure 10:
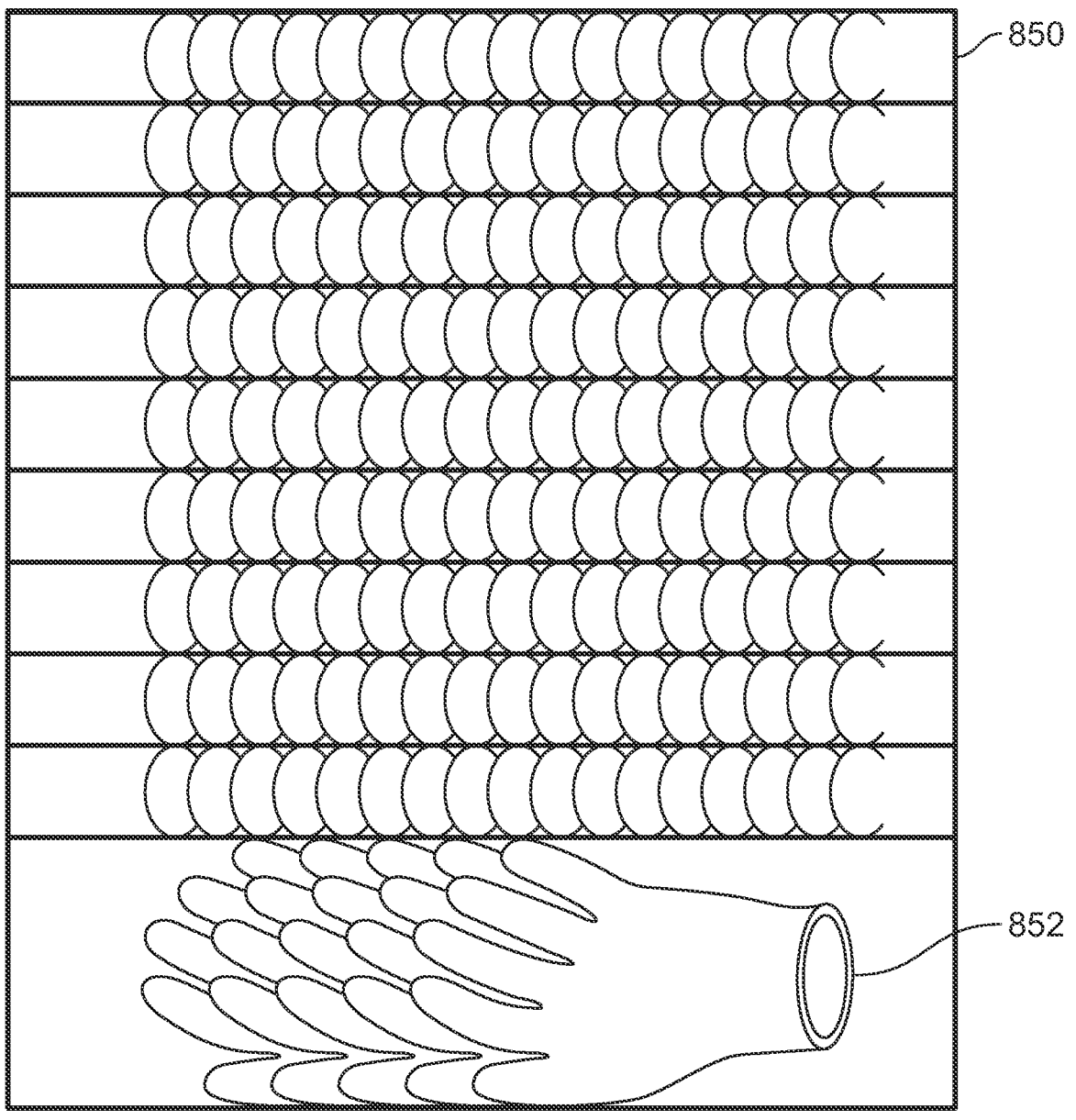
FIG. 10 is a diagrammatic view of an interior of an exemplary disposable glove dispensing system including cartridges of disposable gloves.

FIG. 10 is a diagrammatic view of an interior of another embodiment of a dispensing system. The interior can include multiple compartments 850 each having multiple compressed gloves 852. The compartment 850 can be stacked on top of each other. In some embodiments the compressed gloves 852 can be nestled within each other. For example, the gloves 852 can be disposed one within the next glove 852. In some embodiments, the gloves 852 can be connected to each other by connecting components (similar to those discussed previously) or can be stacked one on top of the other. These compressed glove cartridges can be loaded into the dispensing system after the gloves 852 in the previous cartridge have been depleted.

Figure 11:
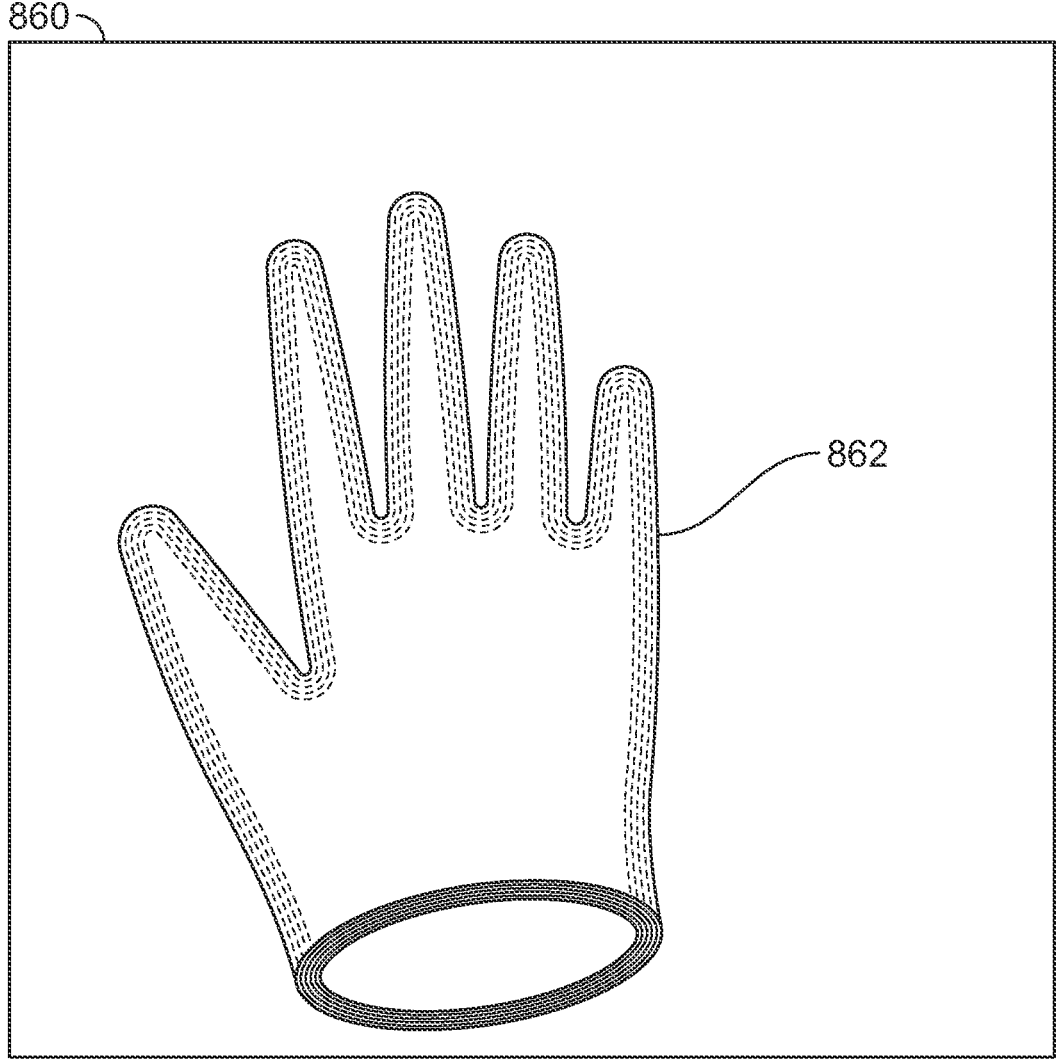
FIG. 11 is a diagrammatic view of packaging of disposable gloves capable of being inserted into a housing of an exemplary disposable glove dispensing system.
Figure 12:
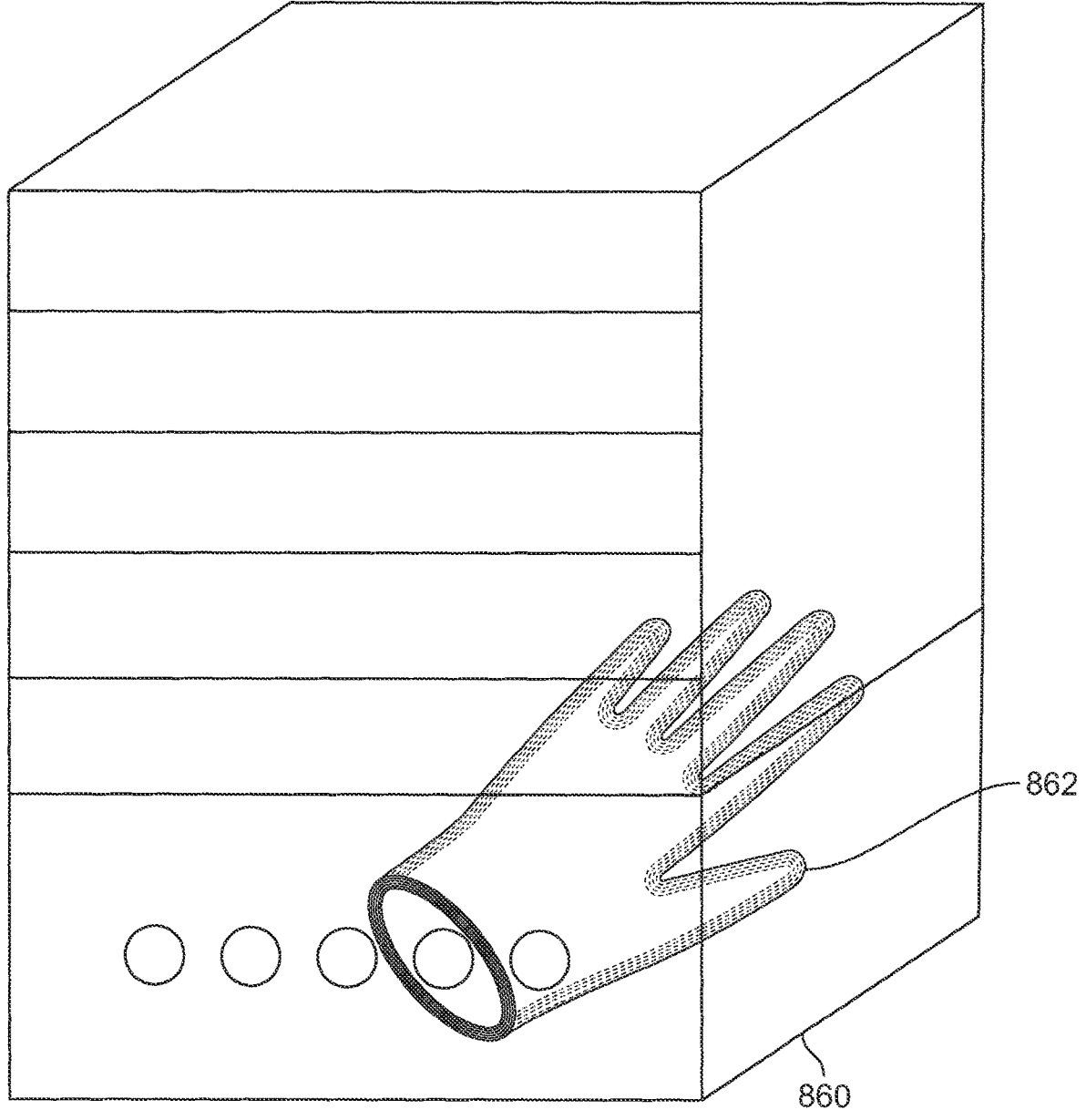
FIG. 12 is a diagrammatic view of an interior of an exemplary disposable glove dispensing system including containers of disposable gloves.

FIG. 11 is a diagrammatic view of another version of a package or cartridge 860 for gloves 862. The gloves 862 can be disposed one within the next glove 862, such that dispensing involves pulling one glove 862 out of the next glove 862 in the cartridge 860. As the user inserts their hand into the glove 862, the glove 862 is transposed onto the user's hands. As the user removes their hand, the glove 862 is separated from the cartridge 860. When the cartridge 860 is empty, it can be removed from the housing and replaced. FIG. 12 illustrates the cartridges 860 of FIG. 11 disposed within a main housing for dispensing disposable gloves. In some embodiments, there can be multiple cartridges 860 which can be stacked on top of each other.

Figure 13:
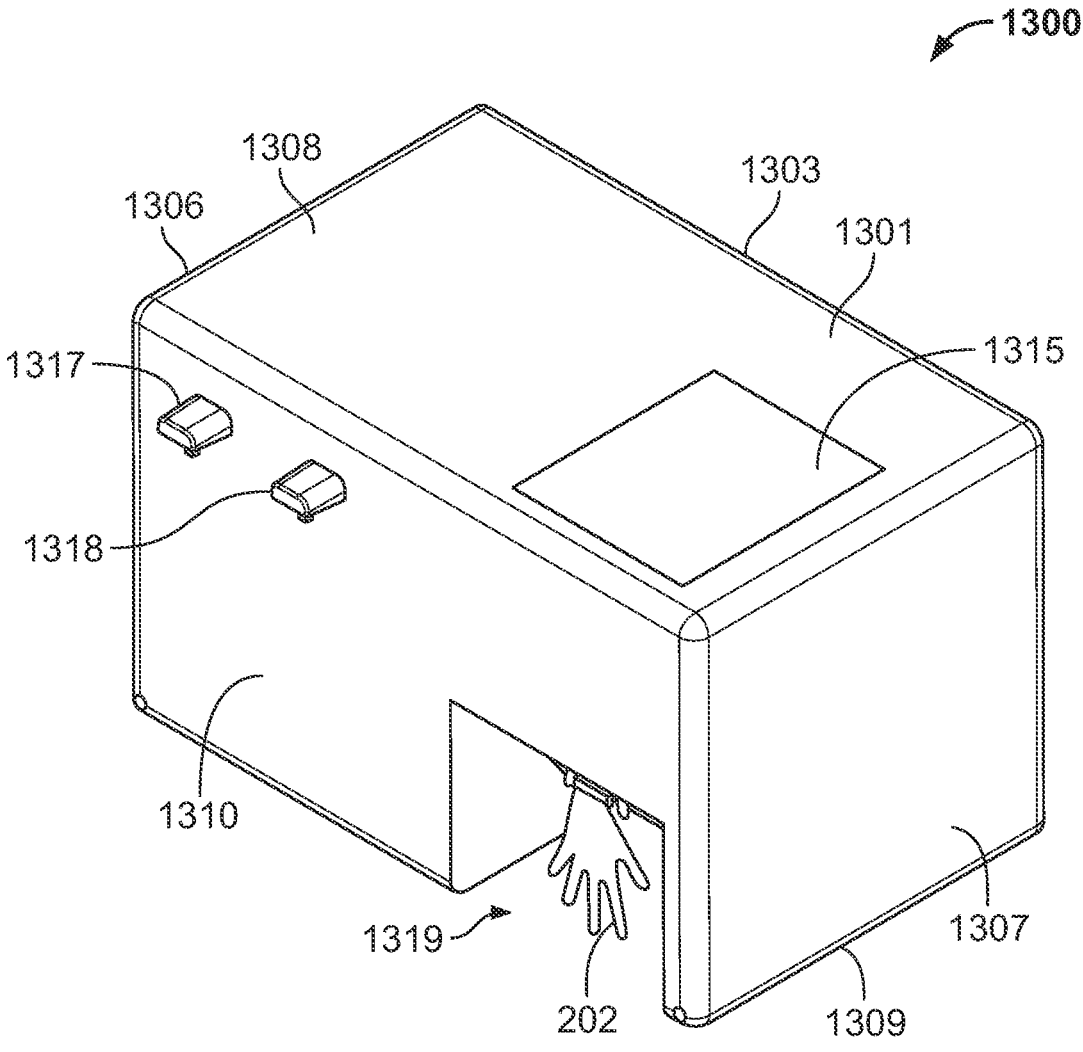
FIG. 13 is a perspective view of an exemplary disposable glove dispensing system of the present disclosure, including a depiction of an exterior of the system with hand-treatment nozzles and a glove dispensing opening.

FIG. 13 shows a perspective view of a disposable glove dispensing system 1300 (hereinafter "system 1300"). The system 1300 can be substantially similar to the systems 100 and/or 300, except for the distinctions noted herein. The system 1300 includes a housing 1301 including a back surface 1303, a first side surface 1306, a second side surface 1307, a top surface 1308, a bottom or base surface 1309, and a front surface 1310. The surfaces may be secured together via fasteners 1322. An opening 1319 is formed on the lower edge of the front surface 1310 and extends to the bottom surface 1309. In some embodiments, the housing 1301 includes an access panel 1315 at the top surface 1308. In some embodiments, the access panel 1315 can be opened or removed to access a fan disposed within the housing 1301. In some embodiments, the access panel 1315 can be opened or removed to enable the gloves 202 to be refilled within the housing 1301. The housing 1301 is configured to at least partially retain and protect internal components discussed herein, and is capable of being selectively mounted to a wall or other similar structures.

The outer portion of the housing 1301 can include one or more a hand-treatment sensors and a glove dispensing sensor. In some embodiments, the sensors can be infrared near-motion detection sensors, photo sensors, or the like. The disposable glove dispensing system 1300 is effected when a user places an object, such as their hand(s), in front of the sensors for actuation of the internal mechanisms of the housing 1301. The housing 1301 can include a cylinder or container 1302, 1316 that includes dispensing hand-treatments, such as moisturizer and/or hand sanitizer. One or more sensors can activate a solenoid or similar mechanism to dispense the hand-treatment. Another sensor can activate a glove dispensing mechanism to dispense a predetermined length of a glove 202. The dispensing mechanism can have an electric circuitry associated therewith for operation of the roll 1325 of gloves 202. The container 1302, 1316 can be replaceable or refillable. The top surface 1308 of the housing 1301 can include a fan capable of being actuated to introduce air into the housing 1301 through an air duct 1326. The air duct 1326 is positioned within the interior of the housing 1301 with one end connected to the fan and the opposing end formed and directed towards gloves 202 for introducing air into the next glove 202 to be dispensed.

The housing 1301 can include nozzles 1317, 1318 protruding from the front surface 1310 for dispensing the hand-treatments. Each nozzle 1317, 1318 can correspond with a respective container 1302, 1316. The nozzles 1317, 1318 can be a variety of geometric shapes, such as triangular or flattened triangular, square or rounded square, rectangular or rounded rectangular, or cylindrical. Upon activation of the hand treatment sensor, the sensor in turn activates the solenoid to open the cylinder to initiate dispensing of a hand treatment. A plunger 1320, 1321 located within the cylinder can move a predetermined distance to dispense a certain amount of the hand treatment each time.

Figure 14:
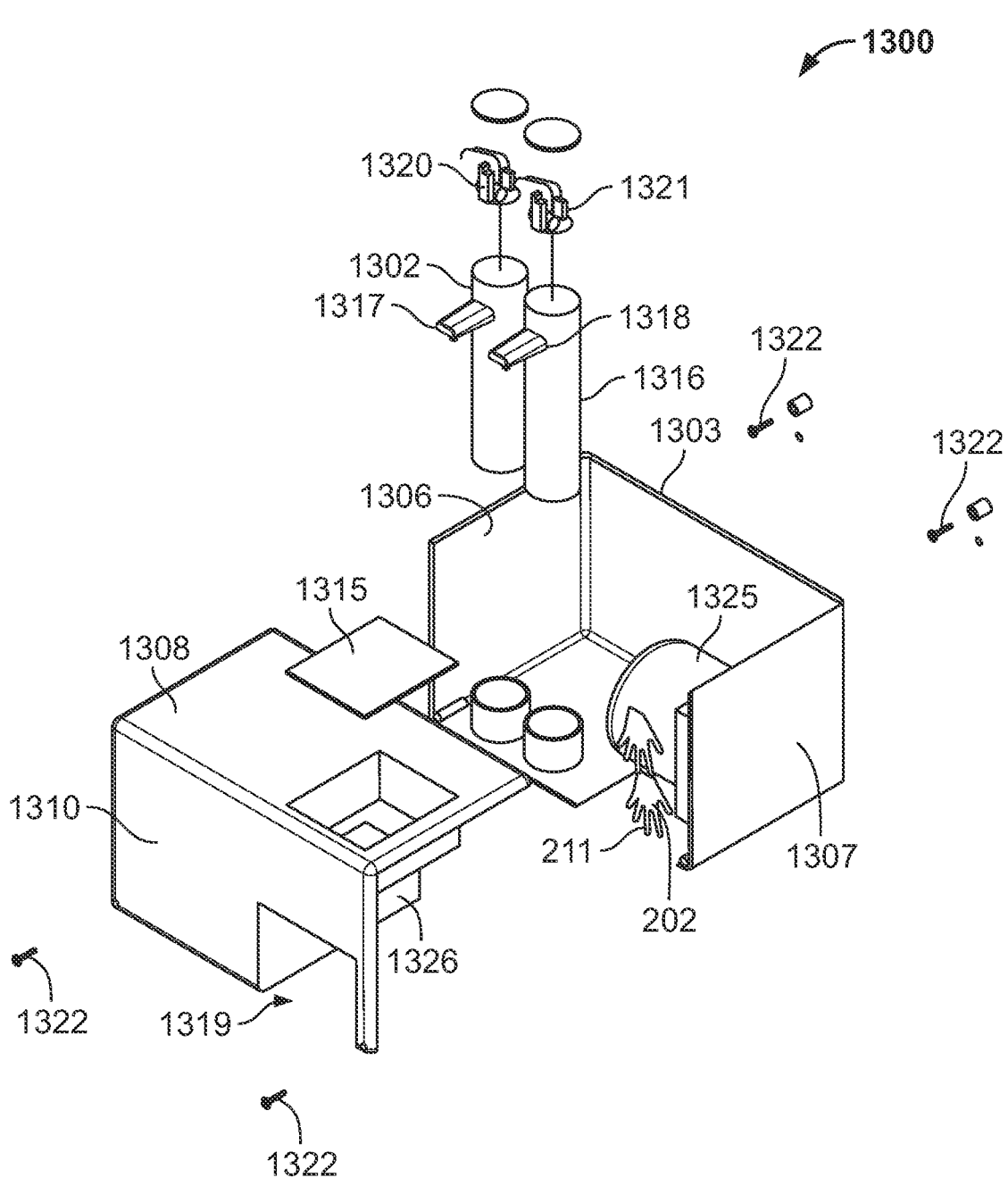
FIG. 14 is a perspective, exploded view of an exemplary disposable glove dispensing system of FIG. 13, illustrating an interior of the system with two cylinders containing the hand-treatment fluid, a roll of disposable gloves disposed within a housing, and a housing opening through which the glove is dispensed.

FIG. 14 shows an exploded interior perspective of the disposable glove dispensing system 1300. Within the housing 1301 are a plurality of gloves 202 disposed around a center support to form a roll 1325. The gloves 202 are dispensed through the opening 1319 positioned on the front/bottom surface 1310, 1309 of the housing 1301, e.g., towards the bottom edge of the front surface 1310. The glove 202 is dispensed in a vertical orientation through the opening 1319, finger sections 211 first, such that the user can move their hand in a downward direction into the glove 202 through the opening 1319. The fan is positioned directly above the roll of gloves 202. When the fan is activated to blow air through the air duct 1326, air is blown into the open wrist section of the glove 202 to partially inflate the glove 202 and allow the user to easily slip their hand inside.

In some embodiments, the system 1300 can include two cylinders 1302, 1316 for independently dispensing of hand-treatments, such as moisturizer and/or hand sanitizer. The system can includes a replaceable or refillable cylinder 1302, 1316 of hand treatments—such as a hand sanitizer and/or a moisturizer—that, when activated, is deposited in the user's hands. In some embodiments, the system 1300 can include one or more sensors that detect the user's hand adjacent to the dispenser for the hand treatment cylinder or canister, such that the sanitizer or moisturizer is dispensed when the user's hand is detected. The touch-free option allows for dispensing of the sanitizer or moisturizer without requiring the user physically touch the dispenser. Upon activation by the hand treatment sensor, the sensor activates the solenoid to open the cylinder 1302, 1316 to initiate dispensing of a hand treatment. Once the hand treatment sensor is activated, the solenoid opens and a plunger 1320, 1321 compresses the hand treatment stored within the appropriate cylinder 1302, 1316 a predetermined distance, thereby dispensing a predetermined amount of the hand treatment out of nozzles 1317, 1318. In some embodiments, the hand treatment can be performed prior to putting on a glove 202. In some embodiments, the hand treatment can be used by the user after the glove 202 has been placed over the hand for additional reassurance of cleanliness.

Figures 15, 16:
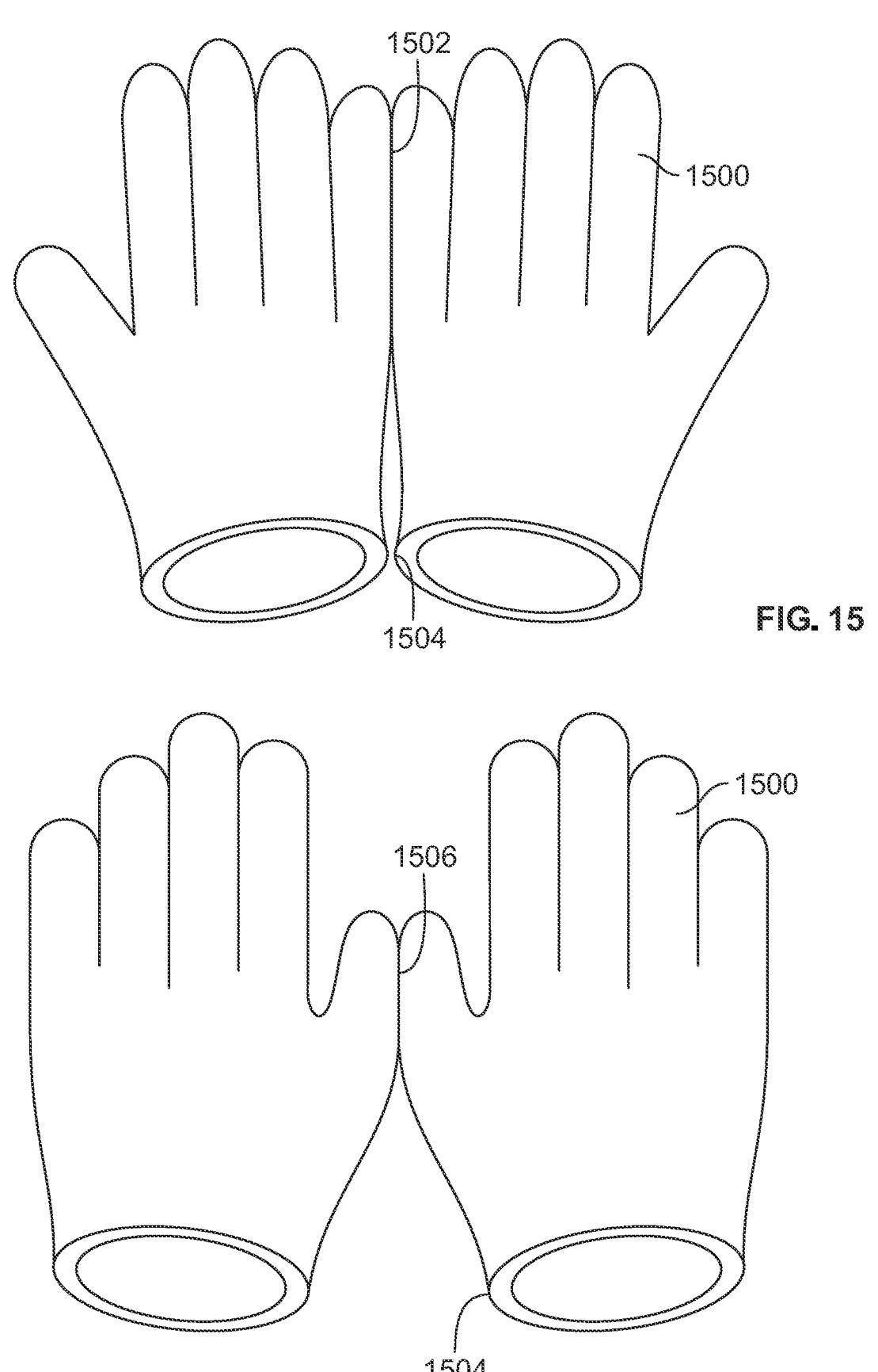
FIG. 15 is a perspective view of disposable gloves connected along a first side of the disposable gloves at a pinkie finger region.
FIG. 16 is a perspective view of disposable gloves connected along a second side of the disposable gloves at a thumb region.

FIGS. 15 and 16 are diagrammatic views of gloves 1500 joined to each other. It should be understood that such connection of gloves 1500 could be used in any of the systems discussed herein. For example, the gloves 1500 can be positioned in a roll form within a housing for selective dispensing. In some embodiments, as shown in FIG. 15, the adjacent gloves 1500 can be connected to each other along at least a portion of the pinkie finger section 1502 (e.g., along the length of the pinkie finger section 1502). In some embodiments, the gloves 1500 can also be connected to each other at a portion of the cuff section 1504. In some embodiments, as shown in FIG. 16, the adjacent gloves 1500 can be connected to each other along at least a portion of the thumb section 1506 (e.g., along the length of the thumb section 1506). In some embodiments, the gloves 1500 can also be connected to each other at a portion of the cuff section 1504. In some embodiments, connection of the gloves 1500 can alternate between the connections shown in FIGS. 15 and 16. For example, the gloves 1500 can initially be connected as shown in FIG. 15, the next adjacent glove 1500 can be connected at the thumb section 1506 as shown in FIG. 16, the subsequent adjacent glove 1500 can be connected again at the pinkie finger section 1502 as shown in FIG. 15, and so on. The connections can be perforated or minimal to allow for easy separation of the gloves 1500 from each other during dispensing.

The present disclosure also relates to the features of the system for dispensing gloves and methods for using such systems. The glove dispensing method can include, but is not limited to, the following steps: the user optionally moisturizes or sanitizes their hand by activating the hand treatment sensor; the solenoid is opened and the plunger is disposed as commanded by the microcontroller; the moisturizer and/or sanitizer is dispensed from the housing. The method can include the steps of: the glove sensor is activated (hand waved over said air sensor); the package of a multitude of gloves stored in roll form is automatically turned to the next available glove as commanded by the microcontroller; fan is activated sending air through air duct; air enters glove ring opening; the glove expands and subsequently is easily grasped by the user and separated from the pre-rolled, glove cartridge.

In some embodiments, the platforms, systems, media, and methods disclosed herein can include software, server, and/or database modules, or use of the same. The software modules disclosed herein are implemented in a multitude of ways. In various embodiments, a software module can include a file, a section of code, a programming object, a programming structure, or combinations thereof. In further various embodiments, a software module can include a plurality of files, a plurality of sections of code, a plurality of programming objects, a plurality of programming structures, or combinations thereof. In various embodiments, the one or more software modules include, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location. For example, in some embodiments, the system can include one or more sensors that detect and transmit when, e.g., hand treatment fluid needs to be replaced, glove supply is running low and needs to be replaced, or the like.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A package of gloves, comprising:
two or more gloves, each of the gloves including a proximal end defining a cuff with an opening capable of receiving a hand of a user therethrough, and a distal end opposing the proximal end and defining finger sections capable of receiving fingers of the hand of the user; and
a removable connecting component disposed between each of the respective gloves and connecting the proximal and distal ends of adjacently disposed gloves to each other;
wherein the removable connecting component is removable from both the proximal and distal ends of the adjacently disposed gloves for separation of the adjacently disposed gloves from each other.

2. The package of gloves of claim 1, wherein the removable connecting component connects each of the two or more gloves to each other such that the two or more gloves define a substantially continuous structure.

3. The package of gloves of claim 1, wherein the two or more gloves are packaged in roll form.

4. The package of gloves of claim 1, wherein the removable connecting component is attached to at least a portion of a perimeter of the cuff at the proximal end and is attached to at least a portion of the finger sections at the distal end.

5. The package of gloves of claim 4, wherein a connection of the removable connecting component to the respective proximal and distal ends is perforated to allow for separation of the removable connecting component from the respective glove.

6. The package of gloves of claim 4, wherein the removable connecting component is attached to only 50% of the perimeter of the cuff at the proximal end.

7. The package of gloves of claim 4, wherein the removable connecting component is attached to only some of the finger sections at the distal end.

8. A system for dispensing gloves, comprising:
a housing including an opening;
gloves disposed within the housing to allow for selective removal of gloves through the opening of the housing, wherein each of the gloves includes a proximal end defining a cuff with an opening capable of receiving a hand of a user therethrough, and a distal end opposing the proximal end and defining finger sections capable of receiving fingers of the hand of the user; and
a removable connecting component disposed between each of the gloves and connecting the proximal and distal ends of adjacently disposed gloves to each other;
wherein the removable connecting component is removable from both the proximal and distal ends of the adjacently disposed gloves for separation of the adjacently disposed gloves from each other.

9. The system of claim 8, comprising a fan disposed above the gloves and including a duct pointing towards the gloves to generate air to partially inflate the glove for the user to don.

10. The system of claim 9, wherein the fan is operable on electric power supplied by batteries or an outlet.

11. The system of claim 8, wherein a connection of the removable connecting component is perforated to allow for separation of the removable connection component from the respective glove.

12. The system of claim 9, comprising an actuating unit mounted on an exterior of the housing and including:

means for detecting a user; and a driving unit connected to the detecting means and activated by the detecting means upon detection of a user;

wherein the fan is coupled to the driving unit such that activation of the driving unit results in air flow from the fan, thereby partially inflating the glove and rotating the gloves a predetermined rotation such that a user can don the glove; and wherein the actuating unit includes a switch means, connected to the driving unit, for deactivating the driving unit after a predetermined amount of time.

13. The system of claim 8, wherein the opening is positioned at the lower portion of a front of the housing, to facilitate the user donning the glove via a downward motion.

14. The system of claim 8, wherein the opening is positioned at the lower portion of a front of the housing and a bottom of the housing to facilitate the user donning the glove via an upward, rightward, or leftward motion relative to the housing.

15. The system of claim 8, comprising at least two containers including hand treatment fluid and capable of being actuated to dispense the hand treatment fluid therefrom.

16. The system of claim 15, wherein each of the containers includes:

an outlet at a bottom of a tubular body;

a plunger within the tubular body;

a blocking member connected to the plunger; and a securing mechanism on a back of the tubular body, securing the tubular body to an interior back wall of the housing.

17. The glove dispenser of claim 16, wherein an actuating unit mounted on an exterior of the housing includes:

means for detecting a user; and a driving unit connected to the detecting means and activated by the detecting means upon detection of a user;

wherein the tubular body is coupled electronically to the driving unit such that activation of the driving unit results in reciprocal linear movement of the plunger, thereby moving the blocking member and dispensing a predetermined amount of the hand treatment through the outlet; and wherein the actuating unit includes switch means, connected to said driving unit, for deactivating said driving unit when the plunger completes one cycle of the reciprocal linear movement.

18. The method of claim 17, comprising motioning a hand in front of an actuating unit of the housing to dispense a predetermined amount of a hand treatment from a container stored within the housing.

19. A method for dispensing gloves, comprising:

at least partially extending a glove from an opening in a housing, the housing including (i) two or more gloves, wherein each of the gloves includes a proximal end defining a cuff with an opening capable of receiving a hand of a user therethrough, and a distal end opposing the proximal end and defining finger sections capable of receiving fingers of the hand of the user, and (ii) a removable connecting component disposed between each of the respective gloves and connecting the proximal and distal ends of adjacently disposed gloves to each other, wherein the removable connecting component is removable from both the proximal and distal ends of the adjacently disposed gloves for separation of the adjacently disposed gloves from each other; and separating the glove from the removable connecting component to fully remove the glove from the housing.

20. The method of claim 19, motioning a hand in front of an actuating unit of the housing to activate extension of the glove from the housing and to expose a majority of the glove.

21. A system for dispensing gloves, comprising:

a housing including an opening;

gloves disposed within the housing to allow for selective removal of gloves through the opening of the housing, wherein each of the gloves includes a proximal end defining a cuff with an opening capable of receiving a hand of a user therethrough, and a distal end opposing the proximal end and defining finger sections capable of receiving fingers of the hand of the user;

a removable connecting component disposed between each of the gloves and connecting the proximal and distal ends of adjacently disposed gloves to each other; and a fan disposed above the gloves and including a duct pointing towards the gloves to generate air to at least partially inflate the glove.

22. A method for dispensing gloves, comprising:

at least partially extending a glove from an opening in a housing, the housing including (i) two or more gloves, wherein each of the gloves includes a proximal end defining a cuff with an opening capable of receiving a hand of a user therethrough, and a distal end opposing the proximal end and defining finger sections capable of receiving fingers of the hand of the user, and (ii) a removable connecting component disposed between each of the respective gloves and connecting the proximal and distal ends of adjacently disposed gloves to each other;

generating air with a fan disposed above the two or more gloves, the fan including a duct pointing towards the two or more gloves to at least partially inflate one of the gloves; and separating the glove from the removable connecting component to fully remove the glove from the housing.

\* \* \* \* \*